United States Patent
Ostergren

(10) Patent No.: US 9,678,043 B2
(45) Date of Patent: Jun. 13, 2017

(54) METHODS, SYSTEMS, AND FIXTURES FOR INSPECTION OF GASKET WELDS

(71) Applicant: BP Corporation North America Inc., Naperville, IL (US)

(72) Inventor: Kevin Ostergren, Midland, MI (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/939,098

(22) Filed: Nov. 12, 2015

(65) Prior Publication Data

US 2017/0138909 A1    May 18, 2017

(51) Int. Cl.
*G01N 29/07*    (2006.01)
*G01N 29/22*    (2006.01)

(52) U.S. Cl.
CPC .......... *G01N 29/223* (2013.01); *G01N 29/07* (2013.01); *G01N 2291/267* (2013.01)

(58) Field of Classification Search
CPC ............................ G01N 29/223; G01N 29/07
USPC .......................................................... 73/588
See application file for complete search history.

(56) References Cited

U.S. PATENT DOCUMENTS

| 4,102,206 A * | 7/1978 | Perdijon ................. G01N 29/28 73/623 |
| 4,856,321 A * | 8/1989 | Smalling ................. G01F 1/662 73/40.5 A |
| 5,804,730 A | 9/1998 | Pfannenstiel et al. |
| 6,530,278 B1 * | 3/2003 | Bowersox .............. B23K 31/12 73/623 |
| 7,021,143 B2 | 4/2006 | Dasch |
| 7,412,890 B1 * | 8/2008 | Johnson ............... G21C 17/007 73/618 |
| 7,496,456 B2 | 2/2009 | Hiyama et al. |
| 7,698,946 B2 | 4/2010 | Clarke et al. |

(Continued)

FOREIGN PATENT DOCUMENTS

| CN | 203551515 | 4/2014 |
| JP | 60060555 | 4/1985 |

(Continued)

OTHER PUBLICATIONS

Oceaneering Inspection, "Flange Face Inspection Gets the "Seal" of Approval From BP," Feb. 2011, pp. 6-7.

(Continued)

*Primary Examiner* — J M Saint Surin
(74) *Attorney, Agent, or Firm* — Kelly L. Cummings

(57) ABSTRACT

A method may involve positioning a fixture over a portion of a tube portion of a gasket, where the gasket includes a first lip portion joined to a second lip portion by a weld of the gasket and the first lip portion joined to the second lip portion defines the tube portion, where the fixture comprises a housing and an injection port; positioning an ultrasonic probe in the housing; filling, by the injection port, coupling fluid between the ultrasonic probe and the tube portion of the gasket; and scanning at least a portion of the weld with the ultrasonic probe, where scanning the at least a portion of the weld may involve transmitting, by the ultrasonic probe, a plurality of ultrasonic waves through the coupling fluid into the tube portion, and translating the fixture in a longitudinal direction along the tube portion of the gasket.

20 Claims, 12 Drawing Sheets

(56) References Cited

U.S. PATENT DOCUMENTS

| | | | |
|---|---|---|---|
| 9,037,419 | B2 | 5/2015 | Na et al. |
| 2009/0320601 | A1 | 12/2009 | Kleinert |
| 2011/0000302 | A1* | 1/2011 | Deleye .................. G01N 29/07 73/637 |
| 2011/0166807 | A1 | 7/2011 | Kitazawa et al. |
| 2013/0028478 | A1 | 1/2013 | St-Pierre et al. |
| 2014/0076053 | A1 | 3/2014 | Gaudet et al. |
| 2014/0102201 | A1 | 4/2014 | Brignac et al. |
| 2014/0184750 | A1 | 7/2014 | Thigpen et al. |
| 2014/0238136 | A1 | 8/2014 | Ten Grotenhuis et al. |
| 2015/0039245 | A1 | 2/2015 | Langlois et al. |

FOREIGN PATENT DOCUMENTS

| | | |
|---|---|---|
| JP | 06174579 | 6/1994 |
| JP | 07191002 | 7/1995 |
| WO | WO 2012/167380 | 12/2012 |

OTHER PUBLICATIONS

Sankar, "Evaluation of Flange Face Corrosion Using Phased Array Ultrasonic Testing (PAUT) in Process Industry," International Journal of Current Research, pp. 493-500, Mar. 2013.

Tecscan, "Challenges of Performing Automated Ultrasonic Inspection," Feb. 23, 2015.

Michael Moles, "Portable Phased Array Applications," 3rd MENDT, Nov. 27-30, 2005, Bahrain, Manama, 18 pages.

Nugent et al., "Refining Industry Experience with HF Unit Flange Face Corrosion and Detection for API RP 751," NACE Corrosion Conference & Expo, 2011, pp. 1-11.

Moles et al., "Pipeline Girth Weld Inspections Using Ultrasonic Phased Arrays," Proceedings of PVP2003, Jul. 20-24, 2003, Cleveland, OH, pp. 1-9.

Ciorau et al., "3-D Data Plotting: A Useful Tool for PAUT," NDT.net—The e-Journal of Nondestructive Testing (Jul. 2008), 10 pages.

Moles et al., "Linear Inspection of Welds Using Ultrasonic Phased Arrays," Proceedings of the 7th International Conf., May 16-20, 2005, pp. 319-325.

Wu et al., "Flaw Imaging Device for Ultrasonic Inspection of Thick Welds," 7th International Conf. on NDE in the Nuclear Industry, Grenoble, Jan./Feb. 1985, pp. 249-252.

Pugalendhi et al., "Use of Phased Array Testing (PAUT) & Time of Flight Diffraction (TOFD) in Lieu of Radiology Testing . . .," SINCE2013, Jul. 19-20, 2013, pp. 1-14.

Michael Moles, "Ultrasonic Phased Arrays of Weld Inspections," AIP Conference Proceedings, 615, 902 (2002), pp. 902-907.

\* cited by examiner

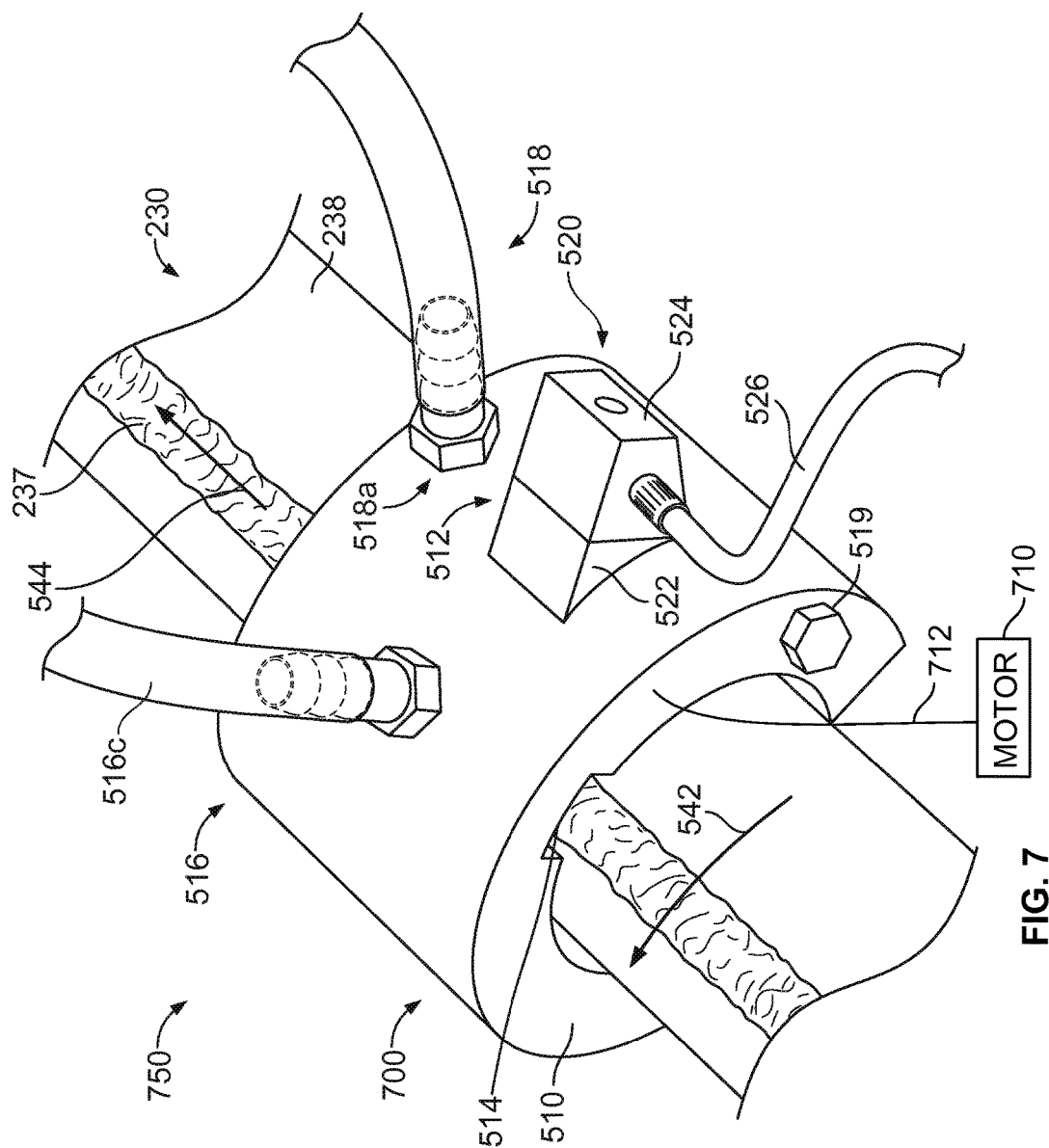

METHODS, SYSTEMS, AND FIXTURES FOR INSPECTION OF GASKET WELDS

FIELD OF THE INVENTION

The disclosure is directed to the testing the integrity of gasket welds.

BACKGROUND OF THE INVENTION

Equipment, such as equipment used in a process facility, may include a pair of flanges and a gasket between the pair of flanges. Such gaskets may include a weld, and the weld may be inspected using nondestructive testing techniques.

SUMMARY OF THE INVENTION

In one aspect, a method is disclosed. The method may involve positioning a fixture over a portion of a tube portion of a gasket, where the gasket includes a first half and a second half, where the first half includes a first planar portion and a first lip portion, and the second half includes a second planar portion and a second lip portion, where the first planar portion is welded to a first flange, where the second planar portion is welded to a second flange, where the first lip portion is joined to the second lip portion by a weld of the gasket and the first lip portion joined to the second lip portion defines the tube portion of the gasket, where the fixture comprises a housing and an injection port; positioning an ultrasonic probe in the housing, such that the ultrasonic probe is located at an angle from the weld; filling, by the injection port, coupling fluid between the ultrasonic probe and the tube portion of the gasket; and scanning at least a portion of the weld of the gasket with the ultrasonic probe, wherein scanning the at least a portion of the weld involves transmitting, by the ultrasonic probe, a plurality of ultrasonic waves through the coupling fluid into the tube portion of the gasket, and translating the fixture in a longitudinal direction along the tube portion of the gasket.

In another aspect, a method is disclosed, where the first flange is coupled to a shell portion of a heat exchanger, and wherein the second flange is coupled to a channel portion of the heat exchanger.

In another aspect, a method is disclosed, where the weld includes a seal weld.

In another aspect, a method is disclosed, where the ultrasonic probe includes an ultrasonic phased array probe, and where the ultrasonic phased array probe includes a wedge and a transducer.

In another aspect, a method is disclosed, where positioning an ultrasonic probe in the housing involves positioning the wedge in the housing.

In another aspect, a method is disclosed, where the ultrasonic probe is positioned closer to the second flange than the first flange.

In another aspect, a method is disclosed, where the coupling fluid includes water.

In another aspect, a method is disclosed, where scanning the weld further includes rotating the fixture in a circumferential direction along the tube portion of the gasket.

In another aspect, a method is disclosed, where rotating the fixture in the circumferential direction includes rotating the fixture in the circumferential direction around 0.600 inches.

In another aspect, a method is disclosed, where rotating the fixture in the circumferential direction includes rotating the fixture counterclockwise toward the first flange.

In another aspect, a method is disclosed, where scanning the weld further includes rotating the fixture in a second circumferential direction opposite the circumferential direction.

In another aspect, a method is disclosed, where translating the fixture in the longitudinal direction along the tube portion includes translating the fixture in the longitudinal direction around 0.500 inches.

In another aspect, a method is disclosed, where the fixture is coupled to a motor, and wherein rotating the fixture in the circumferential direction includes rotating the fixture in the circumferential direction with the motor.

In another aspect, a method is disclosed, where the fixture is coupled to a motor, and wherein translating the fixture in the longitudinal direction includes translating the fixture in the longitudinal direction with the motor.

In another aspect, a method is disclosed, where the method may further involve determining a defect in the at least a portion of the weld of the gasket based on scanning the at least portion of the weld with the ultrasonic probe.

In another aspect, a system is disclosed. The system may include a fixture positioned over a portion of a tube portion of a gasket, where the gasket includes a first half and a second half, where the first half includes a first planar portion and a first lip portion, and the second half includes a second planar portion and a second lip portion, where the first planar portion is welded to a first flange, where the second planar portion is welded to a second flange, where the first lip portion is joined to the second lip portion by a weld of the gasket and the first lip portion joined to the second lip portion defines the tube portion of the gasket, where the fixture includes a housing, a rotational guide, and an injection port; and an ultrasonic probe positioned in the housing, where the fixture is configured to rotate in a circumferential direction along the tube portion of the gasket via the rotational guide, and where the fixture is configured to translate in a longitudinal direction along the tube portion of the gasket.

In another aspect, a system is disclosed, where the weld includes a seal weld.

In another aspect, a system is disclosed, where the ultrasonic probe includes an ultrasonic phased array probe.

In another aspect, a system is disclosed, where the system further includes a motor coupled to the fixture, where the fixture is configured to rotate in the circumferential direction along the tube portion of the gasket via the rotational guide by the motor.

In another aspect, a fixture is disclosed. The fixture may include a housing; an injection port; and a rotational guide, where the fixture is configured to be positioned over a portion of a tube portion of a gasket, where the gasket includes a first half and a second half, where the first half includes a first planar portion and a first lip portion, and the second half includes a second planar portion and a second lip portion, where the first planar portion is welded to a first flange, where the second planar portion is welded to a second flange, where the first lip portion is joined to the second lip portion by a weld of the gasket and the first lip portion joined to the second lip portion defines the tube portion of the gasket, where the fixture is configured to rotate in a circumferential direction along the tube portion of the gasket via the rotational guide, and where the fixture is configured to translate in a longitudinal direction along the tube portion of the gasket.

BRIEF DESCRIPTION OF THE DRAWINGS

The accompanying drawings, which are included to provide a further understanding of the disclosure, are incorporated in and constitute a part of this specification, illustrate embodiments of the disclosure, and together with the detailed description serve to explain the principles of the invention. No attempt is made to show structural details of the invention in more detail than may be necessary for a fundamental understanding of the invention and various ways in which it may be practiced.

FIG. 7 shows a fixture positioned over a portion of a tube portion of a gasket, according to an example embodiment.

DETAILED DESCRIPTION OF THE INVENTION

Methods, systems, and fixtures for inspection of gasket welds are described herein. In particular, embodiments may take the form of or relate to a fixture that includes a housing and a rotational guide. An ultrasonic probe may be positioned in the housing.

In an illustrative implementation, the fixture may be positioned over a tube portion of a gasket. The gasket may include a first half and a second half. Moreover, the first half may include a first planar portion and a first lip portion, and the second half may include a second planar portion and a second lip portion. Further, the first planar portion may be welded to a first flange, the second planar portion may be welded to a second flange, the first lip portion may be joined to the second lip portion by a weld of the gasket, and the first lip portion joined to the second lip portion may define the tube portion of the gasket. The first and second flanges may be associated with equipment used in a process facility.

In addition, in some implementations, the weld of the gasket may be scanned with the ultrasonic probe. The scanning of the weld may involve transmitting, by the ultrasonic probe, a plurality of ultrasonic waves into the tube portion of the gasket, and translating the fixture in a longitudinal direction along the tube portion of the gasket. Moreover, in some implementations, the scanning may further involve rotating the fixture in a circumferential direction at various points along the tube portion of the gasket. The fixture may be configured to rotate in the circumferential direction via the rotational guide.

Beneficially, embodiments described herein may improve ultrasonic scanning of the weld of the gasket. For instance, embodiments described herein may improve scanning coverage of the weld, which may in turn improve detection of defects (or flaws) in the weld of the gasket. By improving detection of defects in the weld of the gasket, fluid leaks between the first and second flanges during operation of the equipment may be reduced, which may in turn improve the reliability of the equipment and/or safety of a person near the equipment.

EXAMPLES

Example 1

Equipment

Figure 1:
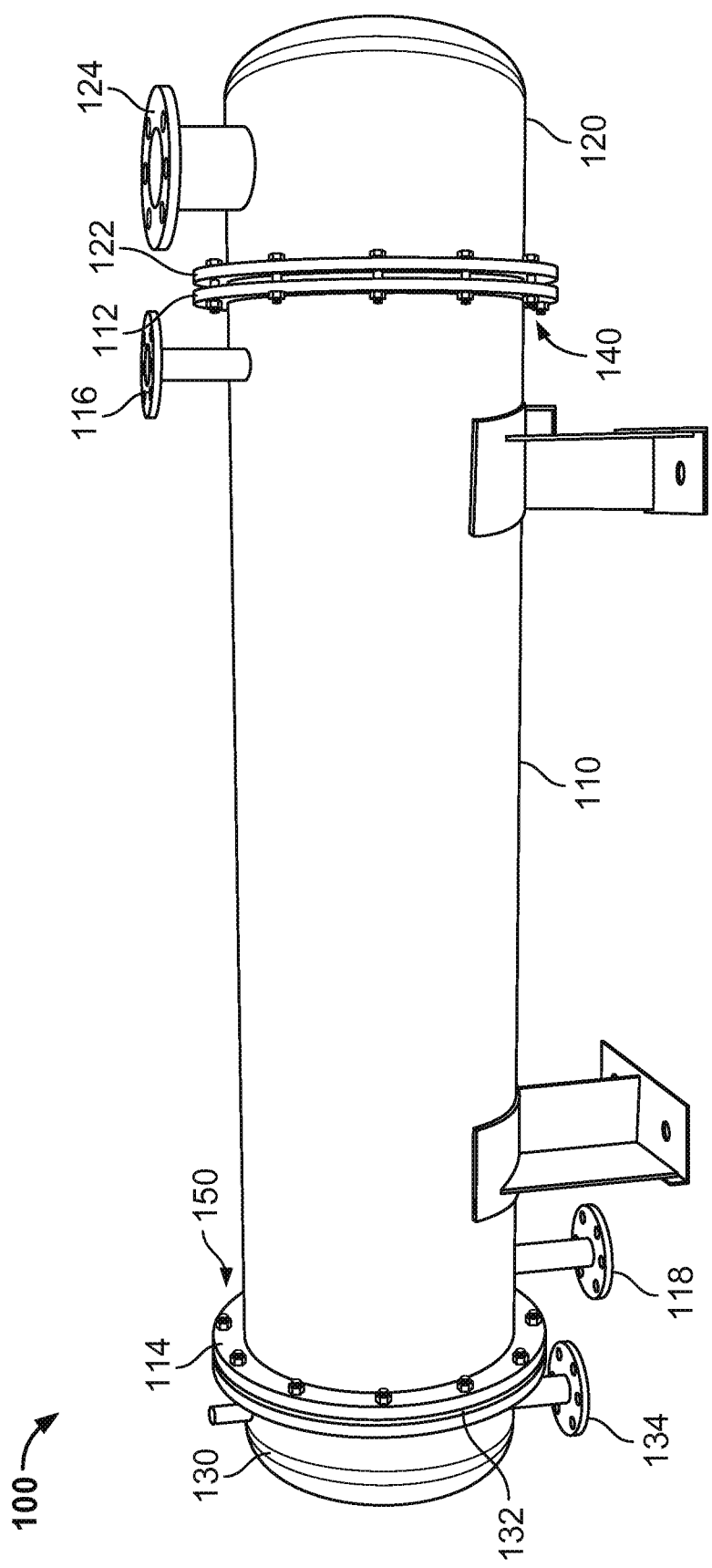
FIG. 1 shows a heat exchanger, according to an example embodiment.

FIG. 1 shows a heat exchanger 100, according to an example embodiment. The heat exchanger 100 may include a shell 110, a first channel (or floating head) 120 and a second channel 130. The shell 110 may include a first shell flange 112, a second shell flange 114, a shell inlet 116, and a shell outlet 118. Moreover, the first channel 120 may include a channel flange 122, and a channel outlet 124. Further, the second channel 130 may include a channel flange 132, and a channel inlet 134.

In some embodiments, the heat exchanger 100 may be configured to transfer heat between two fluids. For example, the heat exchange 100 may take the form of a shell and tube exchanger and may include a tube bundle (not shown). The tube bundle may extend between the first channel 120 and the second channel 130 and may be surrounded by the shell 110, the first channel 120, and the second channel 130. In such examples, the heat exchanger 100 may be configured to transfer heat between: (i) a tube-side fluid that flows from the channel inlet 134 to the channel outlet 124 through the tube bundle, and (ii) a shell-side fluid that flows from the shell inlet 116 to the shell outlet 118 over the tube bundle.

The tube-side fluid and the shell-side fluid may each take various different forms in various different embodiments. In some embodiments, the heat exchanger 100 may be located in an oil refinery, and the tube-side fluid and/or the shell-side fluid may include various forms of petroleum, such as gas oil. However, in other embodiments, the heat exchanger may be located in various other process facilities, such as a chemical plant or a power plant (e.g., fossil fuel power plant or nuclear energy power plant), and the tube-side fluid and shell-side fluid may include any suitable process fluid.

Moreover, as shown in FIG. 1, the first shell flange 112 may be coupled to the channel flange 122 by a first plurality of fasteners 140, and the second shell flange 114 may be coupled to the channel flange 132 by a second plurality of fasteners 150. The first plurality of fasteners 140 and the second plurality of fasteners 150 may include any suitable fastener configured to couple a shell flange (e.g., the first shell flange 112) to a channel flange (e.g., the channel flange 122), such as a bolt with nuts.

In some embodiments, a first gasket (not shown) may be disposed between the first shell flange 112 and the channel flange 122, and a second gasket (not shown) may be disposed between the second shell flange 114 and the channel flange 132. Moreover, in some embodiments, the combination of a gasket disposed between a first flange and second flange may be referred to as a gasket joint.

During operation of the heat exchanger 100, the first gasket may reduce fluid leaks (e.g., tube-side fluid and/or shell-side fluid) between the first shell flange 112 and the channel flange 122, and the second gasket may reduce fluid leaks between the second shell flange 114 and the channel flange 134.

However, the first gasket may include a defect from fabrication and/or installation and/or the result of operational stresses, that might contribute to a fluid leak between the first shell flange 112 and the channel flange 122, and the second gasket may include such a defect that might contribute to a fluid leak between the second shell flange 114 and the channel flange 132. Further, start-up and shut-down of the heat exchanger 100 may cause thermal stresses on components of the heat exchanger 100 that might contribute to a fluid leak between the first shell flange 112 and the channel flange 122 and/or a fluid leak between the second shell flange 114 and the channel flange 132.

Figure 2A:
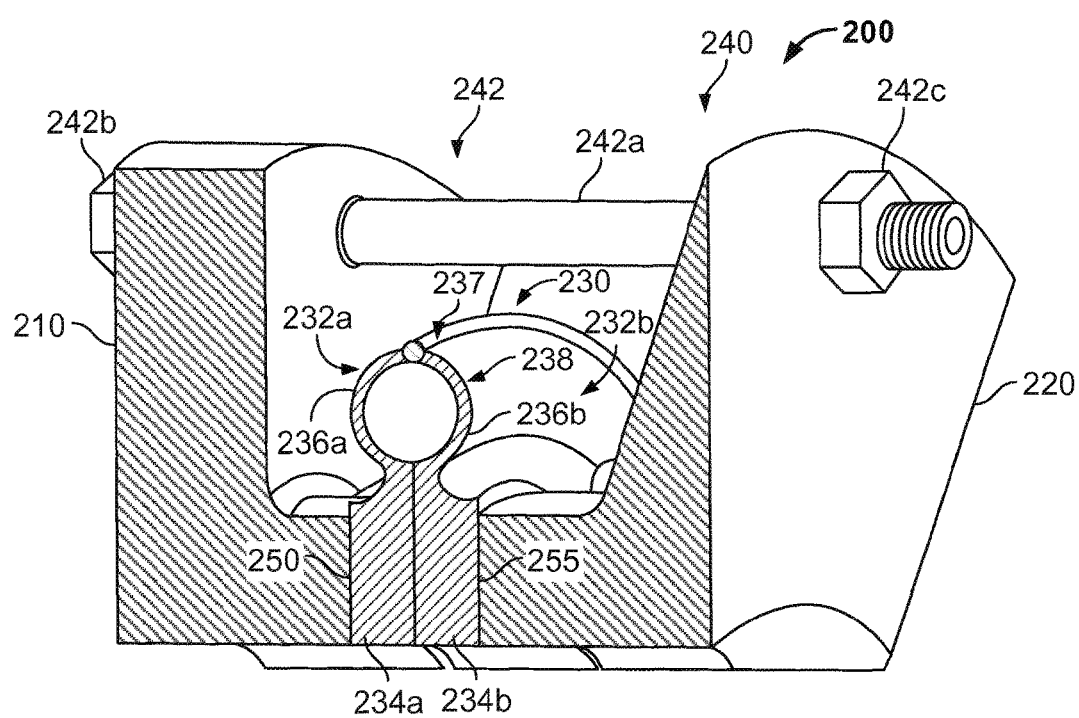
FIG. 2A shows a gasket joint in cross section, according to an example embodiment.

FIG. 2A shows a gasket joint 200 in cross section, according to an example embodiment. The gasket joint 200 may include a first flange 210, a second flange 220, and a gasket 230. As shown in FIG. 2A, the gasket 230 may be disposed between the first flange 210 and the second flange 220. Further, the first flange 210, the gasket 230, and the second flange 220 may be joined by a plurality of fasteners 240. Moreover, as shown in FIG. 2A, the plurality of fasteners may include a first fastener 242. In some embodiments, the first fastener 242 may take the form of a bolt with nuts, and in such embodiments, the first fastener 242 may include a bolt 242a, a first nut 242b, and a second nut 242c.

Further, the gasket 230 may include a first half 232a and a second half 232b. The first half 232a may include a first planar portion 234a and a first lip portion 236a, and the second half 232b may include a second planar portion 234b and second lip portion 236b. The first planar portion 234a may be welded to the first flange 210, and the second planar portion 234b may be welded to the second flange 220. In the illustrated example, weld 250 joins the first planar portion 234a and the first flange 210, and weld 255 joins the second planar portion 234b and the second flange 220. Moreover, the first lip portion 236a may be joined to the second lip portion 236b by a weld 237 of the gasket 230 and the first lip portion 236a joined to the second lip portion 236b defines the tube portion 238 of the gasket 230. In some embodiments, the weld 237 of the gasket 230 may take the form of a seal weld. Moreover, in some embodiments, the first planar portion 234a may be welded to the second planar portion 234b.

Figure 2B:
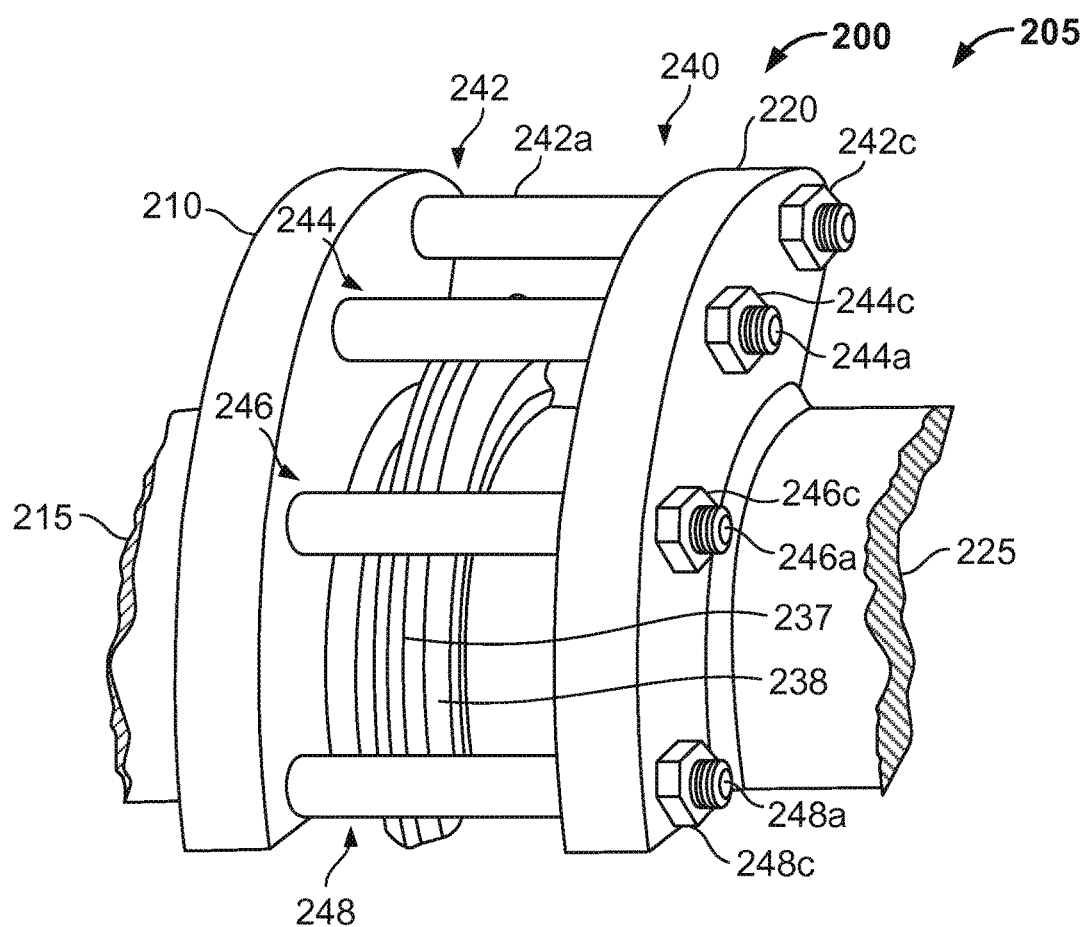
FIG. 2B shows aspects of a gasket joint, according to an example embodiment.

The tube portion 238 of the gasket 230 may extend circumferentially between the first flange 210 and the second flange 220. Similarly, the weld 237 of the gasket 230 may extend circumferentially between the first flange 210 and the second flange 220. FIG. 2B shows aspects of the gasket joint 200, according to an example embodiment. As shown in FIG. 2B, the plurality of fasteners 240 may further include a second fastener 244, a third fastener 246, and a fourth fastener 248. Moreover, as shown in FIG. 2B, the first flange 210 may be coupled to a first portion 215 of equipment 205, and the second flange 220 may be coupled to a second portion 225 of equipment 205.

In some embodiments, the first flange 210 may take the form of or be similar in form to the first shell flange 110, and the second flange 220 may take the form of or be similar in form to the channel flange 122. Accordingly, in some embodiments, the equipment 205 may take the form of or be similar in form to the heat exchanger 100, the first portion 215 of the equipment 205 may take the form of or be similar to the shell 110, and the second portion 225 of the equipment 205 may take the form of or be similar in form to the channel 120. However, in other embodiments, the equipment 205 may take the form of other equipment used in processing facilities, such as a vessel, a tank, piping, etc.

Moreover, in some embodiments, the second fastener 244, third fastener 246, and fourth fastener 248 may take the form of or be similar in form to the first fastener 242. Components of the second fastener 244, third fastener 246, and fourth fastener 248 may have the same arrangement and function in a similar manner as the same or similar numbered components of the first fastener 242.

The tube portion 238 of the gasket 230 may include an outer diameter and an inner diameter. In some embodiments, the outer diameter of the tube portion 238 may be between 210 and 220 millimeters, such as around 216 millimeters. Moreover, in some embodiments, the inner diameter of the tube portion 238 may be between 204 and 216 millimeters, such as around 210 millimeters. Further, the tube portion 238 of the gasket 230 may be hollow.

Moreover, in some embodiments, in response to thermal stress, the tube portion 238 may be configured to deflect. With this arrangement, deflection of the tube portion 238 may contribute to reducing or preventing fluid leaks between the first flange 210 and second flange 220 during operation of the equipment 205. In some embodiments, the gasket 230 may be referred to as a weld-ring gasket. And in some such embodiments, the gasket 230 may include an A24 gasket sold by kempchen & Co. Gmbh. The gasket 230 may include other gaskets sold by kempchen as well, including an A21, A22, A23, or A25 gasket.

Figure 3:
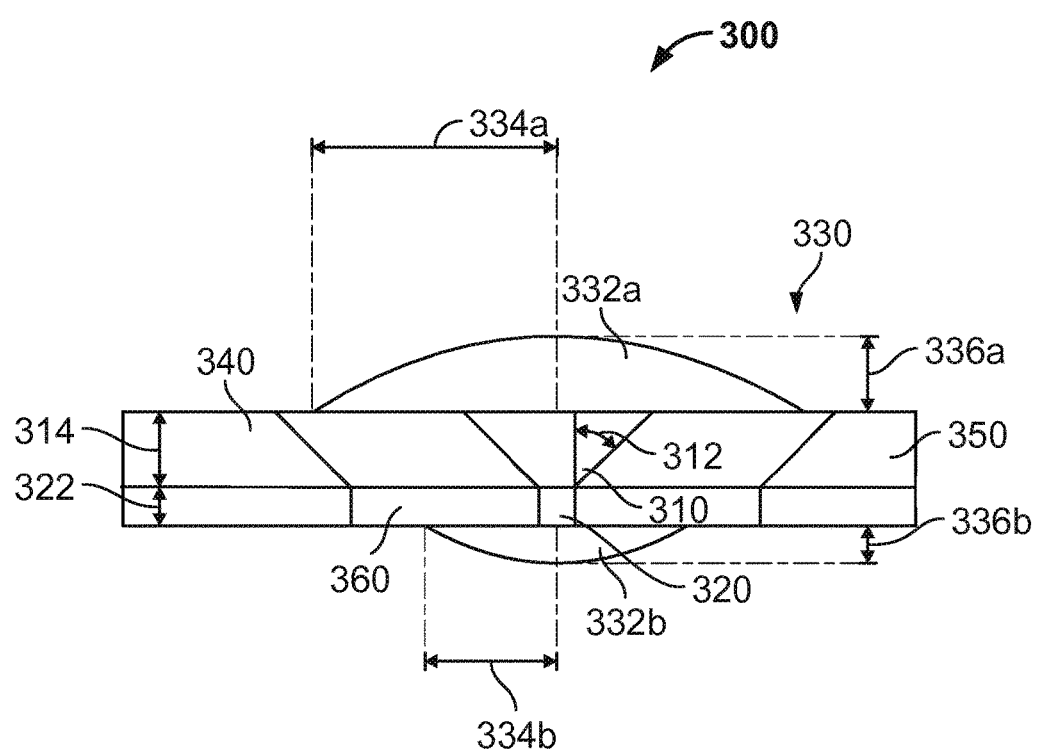
FIG. 3 shows a weld, according to an example embodiment.

FIG. 3 shows a weld 300, according to an example embodiment. The weld 237 may take the form of or be similar in form to the weld 300. The weld 300 may include an upper fill 310, a root 320, and a cap 330. The weld 300 may join a first work piece 340 and a second work piece 350. The first work piece 340 may take the form of or be similar in form to the first lip portion 236a, and the second work piece 350 may take the form of or be similar in form to the second lip portion 236b. In some embodiments, the weld 300 may be a seal weld.

As shown in FIG. 3, the upper fill 310 may include an angle 312 and a height dimension 314. In some embodiments, the angle 312 may be with respect to an axis (not shown) that is substantially perpendicular to the first work piece 340 and the second work piece 350. Moreover, in some embodiments, the angle 312 may be between 40 and 50 degrees, such as 45 degrees. In some embodiments, the angle 312 may take the form of an edge preparation with a gap (or landing) between 0.5 and 1.5 millimeters, such as 1 millimeter. The term "substantially perpendicular," as used in this disclosure, means exactly perpendicular or one or more deviations from exactly perpendicular that do not significantly impact inspection of a weld of a gasket as described herein.

Further, in some embodiments, the height dimension 314 may be between 1 and 3 millimeters, such as 2 millimeters. In addition, the root 320 may include a height dimension 322. In some embodiments, the height dimension 322 may be between 0.5 and to 2 millimeters, such as 1 millimeter. Moreover, in some embodiments, the root 320 may have a width dimension between 0.5 and 3 millimeters, such as 1 millimeter.

Further, in some embodiments, the cap 330 may have a first (top) portion 332a and a second (bottom) portion 332b. The first portion 332a may include a one-half width dimension 334a and a height dimension 336a, and the second portion 332b may include a one-half width dimension 334b and a height dimension 336b. In some embodiments, the one-half width dimension 334a may be between 5 and 7 millimeters, such as 6.5 millimeters. With this arrangement, the first portion 332a may have a width dimension between 10 and 14 millimeters, such as 13 millimeters. Moreover, in some embodiments, the height dimension 336a may be between 1 and 3 millimeters, such as 2 millimeters. Further, in some embodiments, the one-half width dimension 334b may be between 2 and 4 millimeters, such as 3.5 millimeters. With this arrangement, the second portion 332b may have a width dimension between 4 and 8 millimeters, such as 7 millimeters. Further still, in some embodiments, the height dimension 336b may be between 0.5 and 2 millimeters, such as 1 millimeter. In addition, in some embodiments, the first portion 332a may have an overlap dimension between 3 and 5 millimeters, such as 4 millimeters, and the second portion 332b may have an overlap dimension between 2 and 4 millimeters, such as 3 millimeters.

Further still, the weld 300 may have a heat affected zone (HAZ) 360. In some embodiments, the HAZ may have a width between 5 and 10 millimeters, such as 5 millimeters or 10 millimeters.

In some embodiments, the weld 300 may include steel, such as 1020 steel. Moreover, in some embodiments, the weld 300 may include the same or similar material as the first work piece 340 and/or the second work piece 350. Further, in some embodiments, the weld 300 may include or a develop a defect. The defect may take the form of a crack, a void, a discontinuity, or other irregularity in the upper fill 310, the root 320, and/or the cap 300. In some embodiments, the defect may develop during fabrication of the weld 300. Moreover, in some embodiments, when the weld 300 is included in process equipment (e.g., the equipment 205), the defect may develop during operation of the equipment. And in some such embodiments, the defect may develop during start-up or shut-down of the equipment.

Example 2

Fixtures

Figure 4:
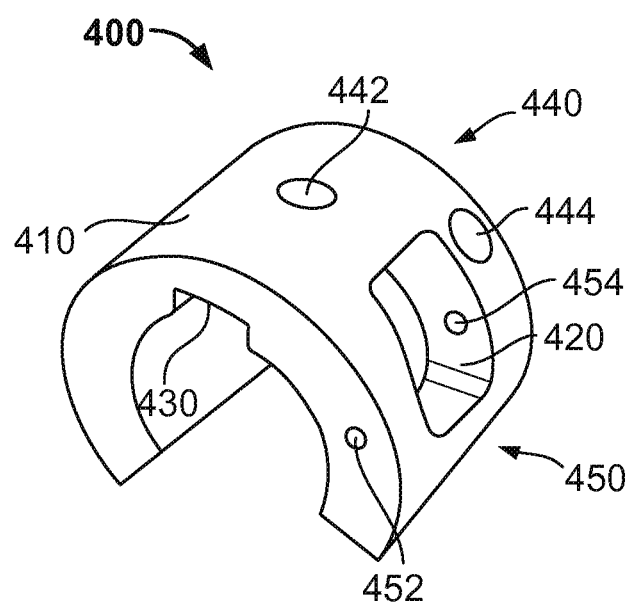
FIG. 4 shows a fixture, according to an example embodiment.

FIG. 4 shows a fixture 400, according to an example embodiment. The fixture 400 may include a body 410, housing 420, a rotational guide 430, injection port holes 440, and positioning holes 450. Further, the injection ports 440 may include a first injection port 442 and a second injection port 444. In addition, the positioning holes 450 may include a first positioning hole 452 and a second positioning hole 454.

The body 410 may be shaped so as to be positioned over a tube portion of a gasket, such as the tube portion 238 of the gasket 230. In some embodiments, the body 410 may include various materials, such as a plastic, a composite, or a metal.

Moreover, the housing 420 may take the form of a cavity through the body 410, and an ultrasonic probe may be positioned in the housing 420. Fasteners may be installed in each of the positioning holes 450 to secure the ultrasonic probe in the housing 420. In some embodiments, the fasteners may take the form of set screws. However, in other embodiments, the fasteners may include any suitable fastener configured to secure the ultrasonic probe in the housing. Further, the rotational guide 430 may take the form of a planar cut-out of the body 410. The fixture 400 may be configured to rotate via the rotational guide 430.

Figure 5:
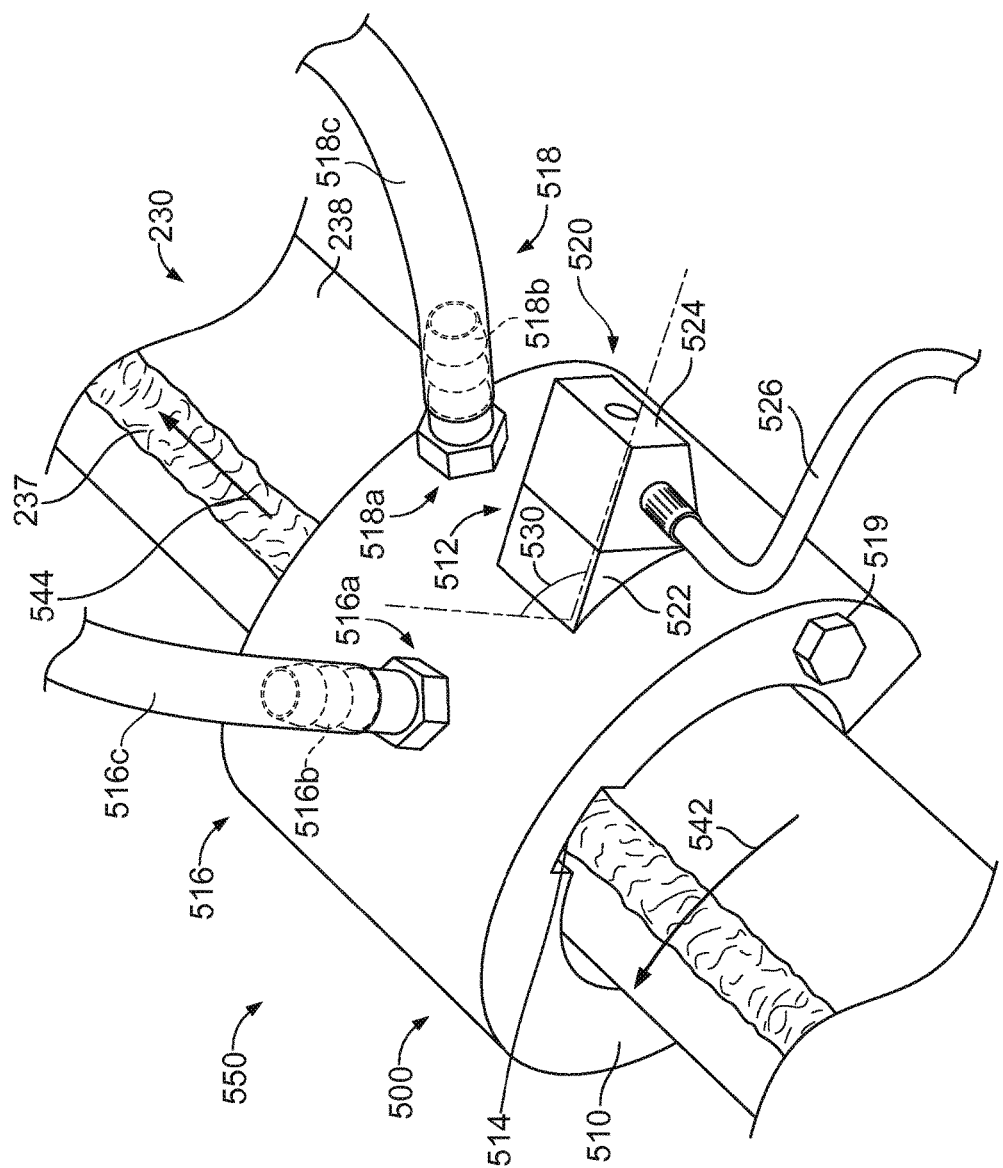
FIG. 5 shows a fixture positioned over a portion of a tube portion of a gasket, according to an example embodiment.

Further still, as shown in FIG. 4, each injection port of the injection ports 440 may include an injection port hole through in the body 410. Each injection port may further include an injection port fitting installed in the injection port through hole and an injection port line installed over the injection port fitting. The injection ports 440 may be configured to provide a coupling fluid to enable the ultrasonic probe to transmit a plurality of ultrasonic waves. For purposes of illustration, injection port fittings and injection port lines are not illustrated in FIG. 4. However, injection port fittings and injection port lines are illustrated in FIG. 5.

In some embodiments, the fixture 400 may be fabricated using one or more dimensions of a first flange (e.g., the first flange 210), a second flange (e.g., the second flange 220), and/or the tube portion of the gasket. For example, the one or more dimensions of the first flange, the second flange, and/or the tube portion may be measured, and the fixture 400 may be fabricated using a three-dimensional printer and the one or more measured dimensions of the first flange, the second flange, and/or the tube portion.

Although the positioning holes 450 are described above as including a first positioning hole 452 and a second positioning hole 454, in other embodiments, a fixture may include more or less than two positioning holes. For example, a fixture may include one positioning hole that may take the form of or be similar in form to the first positioning hole 452.

Further, although the injection ports 440 are described above as including a first injection port 442 and a second injection port 444, in other embodiments, a fixture may include more or less than two injection ports. For example, a fixture may include one injection port that may take the form of or be similar in form to the first injection port 442.

FIG. 5 shows a fixture 500 positioned over a portion of the tube portion 238 of the gasket 230, according to an example embodiment. The fixture 500 may include a body 510, a housing 512, a rotational guide 514, a first injection port 516, and second injection port 518, and a fastener 519. The body 510 may take the form of or be similar in form to the body 410, the housing 512 may take the form of or be similar in form to the housing 420, and the rotational guide 514 may take the form of or be similar in form to the rotational guide 430.

As shown in FIG. 5, an ultrasonic probe 520 may be positioned in the housing 512. The ultrasonic probe 520 may be secured in the housing 512 at least in part by the fastener 519. The ultrasonic probe 520 may further be secured in the housing 512 by a second fastener (not shown). In some embodiments, the fastener 519 may take the form of a set screw. However, in other embodiments, the fastener 519 may be any suitable fastener configured to secure the ultrasonic probe 520 in the housing 512.

The ultrasonic probe 520 may be configured to scan at least a portion of the weld 237. For example, the ultrasonic probe 520 may be configured to transmit a plurality of ultrasonic waves into the tube portion 238 of the gasket 230. At least a portion of the ultrasonic waves transmitted by the ultrasonic probe 520 may be reflected by the weld 237, and the ultrasonic probe 520 may receive the reflected ultrasonic waves.

In some embodiments, the ultrasonic probe 520 may take the form of an ultrasonic phased array probe. Moreover, in some such embodiments, the ultrasonic probe 520 may include an Olympus 10L16 transducer sold by Olympus.

Further, the first injection port 516 may include a first injection port fitting 516b installed in a first injection port hole 516a, and the second injection port 518 may include a second injection port fitting 518b installed in a second injection port hole 518a. In some embodiments, the first injection port fitting 516b and the second injection port fitting 518b may each include a metal, such as brass.

The first injection port 516 and the second injection port 518 may each be configured to provide a coupling fluid between the ultrasonic probe 520 and the tube portion 238 of the gasket 230. With this arrangement, the ultrasonic probe 520 may be configured to transmit a plurality of ultrasonic waves through the coupling fluid into the tube portion 238. In some embodiments, the coupling fluid may include water or glycerin. However, in other embodiments, the coupling fluid may include any suitable fluid configured to transmit ultrasonic waves. Moreover, in some embodiments, the coupling fluid may flow on the tube portion 238 and then flow away from the fixture 500. For example, the coupling fluid may flow away from the fixture 500 via the rotational guide 514 and/or spaces between the tube portion 238 and the body 510.

As shown in FIG. 5, the first injection port 516 may further include a first injection port line 516c coupled to the first injection port fitting 516b, and the second injection port 518 may further include a second injection port line 518c coupled to the second injection port fitting 518c. The first injection port line 516c and the second injection port line 518c may each route a coupling fluid to the first injection port fitting 516b and the second injection port fitting 518b, respectively. In some embodiments, the first injection port line 516c and the second injection port line 518c may each route the coupling fluid from a particular coupling fluid source. However, in other embodiments, the first injection port line 516c may route the coupling fluid from a different coupling fluid source than the second injection portion line 518c.

Further, in some embodiments where the ultrasonic probe 520 includes an ultrasonic phased array probe, the ultrasonic probe 520 may include a wedge 522 and a transducer 524. As shown in FIG. 5, the wedge 522 may be positioned in the housing 512, and the transducer 524 may be positioned on the wedge 522. In some embodiments, the transducer 524 may be fastened to the wedge 552. For example, the transducer 524 may be bolted to the wedge 552.

The wedge 522 may include a surface that contacts the tube portion 238 of the gasket 230 (or the coupling fluid provided by the first injection port 516 and the second injection port 518). In some embodiments, the surface of the wedge 522 that contacts the tube portion 238 may be conformed (or contoured) to a surface of the tube portion 238. Moreover, in some embodiments, the wedge 522 may include a plastic. Further, in some embodiments, the wedge 552 may include a height dimension, a length dimension, a width dimension, and an offset. Further still, in some embodiments, the height dimension of the wedge 552 may be between 5 and 6 millimeters, such as around 5.35 millimeters. Moreover, in some embodiments, the length dimension of the wedge 552 may be between 10 and 12 millimeters, such as around 11.14 millimeters. Further, in some embodiments, the width dimension of the wedge 552 may be between 9 and 11 millimeters, such as around 10.87 millimeters. Further still, in some embodiments, the offset may be between 9 and 11 millimeters, such as around 10.8 millimeters.

The transducer 524 may be configured to transmit a plurality of ultrasonic waves through the wedge 522 and through the coupling fluid provided by the first injection port 516 and the second injection port 518 into the tube portion 238 of the gasket 230. The transducer 524 may have an aperture with a size dimension. In some embodiments, the size dimension may be between 4 and 6 millimeters, such as around 4.96 millimeters. Moreover, in some embodiments, the transducer 524 may include a certain number of transmission elements and the transmission element may each have a pitch dimension. Further, in some embodiments, the transducer 524 may include 16 or 32 transmission elements. Further still, in some embodiments, when the transducer includes 16 transmission elements, the transmission elements may each have a pitch dimension of between 0.25 and 0.5 millimeters, such as around 0.31 millimeters.

In addition, the transducer 524 may be oriented at an angle 530 from a surface of the tube portion 238. In some embodiments, the angle 530 may be between 30 and 40 degrees, such as 33.6 and 36.6 degrees. With this arrangement, the ultrasonic probe 520 may be at an angle from the weld 237. The angle may be based on the angle 530.

Moreover, as shown in FIG. 5, the ultrasonic probe 520 may further include a transmission line 526. The transmission line 526 may be coupled to the transducer 524, and an ultrasonic signal may be routed from the transmission line 526 to the transducer 524.

Further, the rotational guide 514 of the fixture 500 may be disposed over the weld 237 of the gasket 230. The fixture 500 may be configured to rotate in a direction 542 via the rotational guide 514. Further, the fixture 500 may be configured to rotate in a direction that is opposite the direction 542. As shown in FIG. 5, the direction 542 may be a circumferential direction along the tube portion 238 of the gasket 230. Similarly, the direction that is opposite the direction 542 may be a circumferential direction along the tube portion 238.

An amount of rotation of the fixture 500 along the direction 542 and/or along the direction that is opposite the direction 542 may be based at least in part on a width dimension of the rotational guide 514. In some embodiments, the width dimension of the rotational guide 514 may be between 0.400 and 0.800 inches, such as around 0.600 inches. However, in other embodiments, the width dimension of the rotational guide 514 may be more than 0.800 inches or less than 0.400 inches. Further, in some embodiments, the width dimension of the rotational guide 514 may be selected based on scanning the weld 237 with the ultrasonic probe 520. Accordingly, in some embodiments the width dimension of the rotational guide 514 may be selected based at least in part on one or more parameters of the weld 237 and/or the ultrasonic probe 520.

In addition, the fixture 500 may be configured to translate in a direction 544. Further, the fixture 500 may be configured to translate in a direction that is opposite the direction 544. As shown in FIG. 5, the direction 544 may be a longitudinal direction along the tube portion 238 of the gasket 230. Similarly, the direction that is opposite the direction 544 may be a longitudinal direction along the tube portion 238.

One or more dimensions of the fixture 500 may be selected based on one or more dimensions of the first flange 210, the second flange 220, and/or the tube portion 238 of the gasket 230. For example, the one or more dimensions of the first flange 210, the second flange 220, and/or the tube portion 238 of the gasket 230 may be measured, and corresponding dimensions of the fixture 500 may be selected based on the measured dimensions of the first flange 210, the second flange 220, and/or the tube portion 238.

The fixture 500 and the ultrasonic probe 520 may define a system 550.

Although the fixture 500 is described above as including a first injection port 516 and a second injection port 518, in other embodiments, a fixture may include more or less than two injection ports. For example, a fixture may include one injection port that may take the form of or be similar in form to the first injection port 516.

Example 3

Inspection of a Weld of a Gasket

In some embodiments, the weld 237 of the gasket 230 may include or develop a defect that might contribute to a fluid leak between the first flange 210 and the second flange 220 during operation of the equipment 205. Accordingly, it may be desirable to inspect the weld 237 for defects.

FIGS. 6A-6D show an example 600 of inspection of the weld 237 of the gasket 230. In example 600, the fixture 500 may positioned over a portion of the tube portion 238 of the gasket 230, and at least a portion of the weld 237 may be scanned with the ultrasonic probe 520. Example 600 is depicted as a series of four phases 610-640 in FIGS. 6A-D. However, example 600 may be performed in any number of phases or combination of phases. Moreover, for purposes of illustration, aspects of the fixture 500, the first flange 210, the second flange 220, and the gasket 230 in FIGS. 6A-6D are shown in cross section.

Figure 6A:
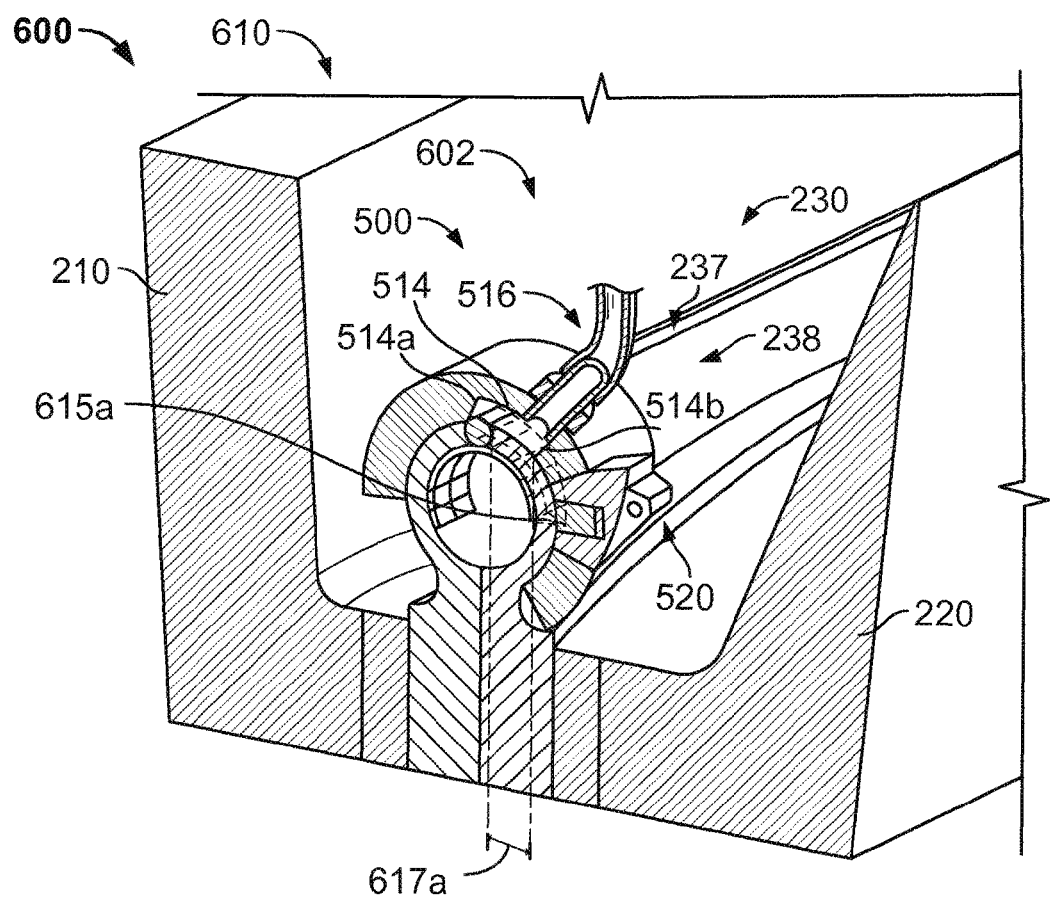
FIG. 6A shows a first phase of an example inspection of a weld of a gasket.

FIG. 6A shows a first phase 610 of the example 600, according to an example embodiment. In the first phase 610, the fixture 500 may be positioned over a portion of the tube portion 238 of the gasket 230 in a first orientation 602. As shown in FIG. 6A, the rotational guide 514 may have a first (left) end 514a and a second (right) end 514b. The first end 514a may be located closer to the first flange 210 than the second flange 220, and the second end 514b may be located closer to the second flange 220 than the first flange 210. In the first orientation 602, the second end 514b may be located a predetermined distance 617a from the weld 237. Moreover, in some embodiments, in the first orientation 602, the first end 514a may contact a portion of the weld 237 (e.g., an edge of the first portion 332a of the cap 330). In some embodiments, the predetermined distance 617a may be between 0.400 and 0.800 inches, such as around 0.600 inches.

Further, at the first phase 610, a coupling fluid (not shown) may be provided by the first injection port 516 and the second injection portion 518 (not shown in FIGS. 6A-6D) between the ultrasonic probe 520 and the tube portion 238 of the gasket 230.

Further still, at the first phase 610, the ultrasonic probe 520 may transmit a plurality of ultrasonic waves 615a through the coupling fluid into the tube portion 238 of the gasket 230. The plurality of the ultrasonic waves 615a may travel in the tube portion 238 through a first portion of the weld 237.

Figure 6B:
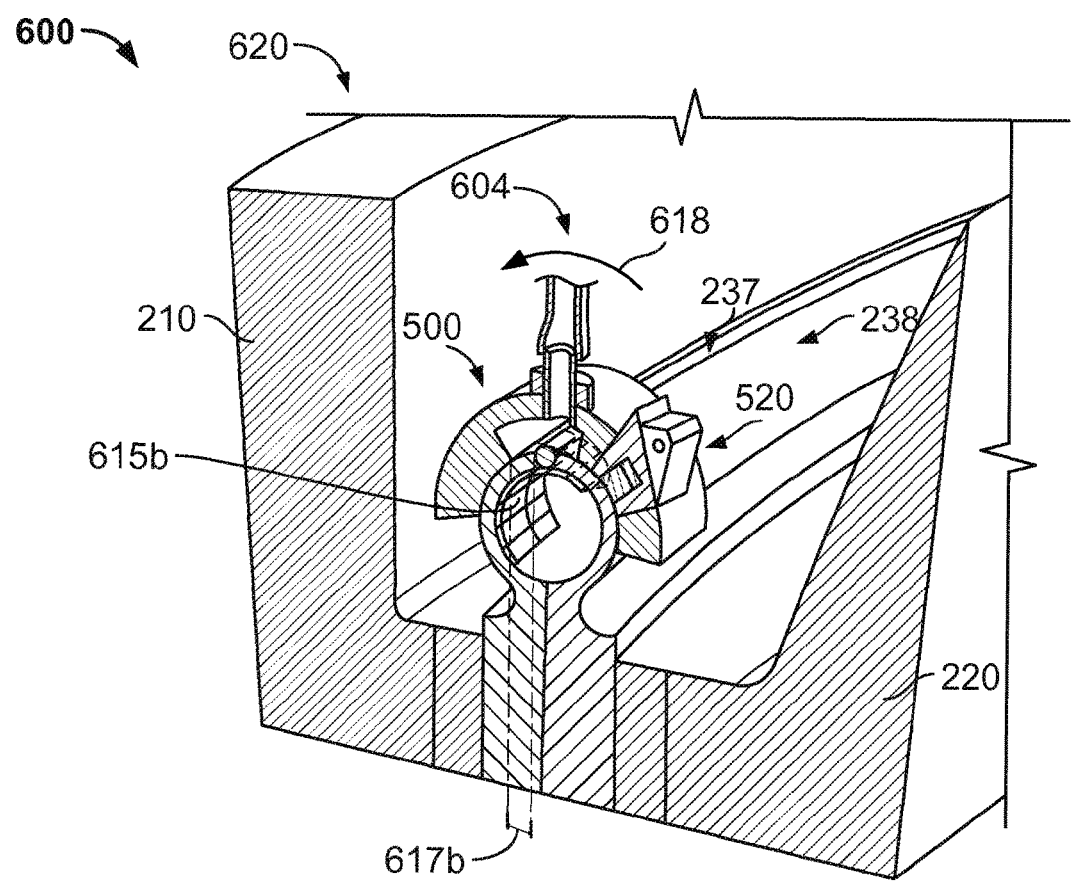
FIG. 6B shows a second phase of an example inspection of a weld of a gasket.

FIG. 6B shows a second phase 620 of the example 600, according to an example embodiment. In the second phase 620, the fixture 500 may be positioned over the portion of the tube portion 238 of the gasket in a second orientation 604. The fixture 500 may be moved from the first orientation 602 to the second orientation 604 by rotating the fixture 500 in a circumferential direction 618 along the tube portion 238. In some embodiments, the fixture 500 may be rotated in the circumferential direction 618 counterclockwise from the second flange 220 toward the first flange 210.

In the second orientation 604, the first end 514a of the rotational guide may be located at predetermined distance 617b from the weld 237. In some embodiments, the predetermined distance 617b may be substantially equal to the predetermined distance 617a. Moreover, in some embodiments, in the second orientation 604 the second end 514b may contact a portion of the weld 237 (e.g., an edge of the first portion 332a of the cap 330). The term "substantially equal," as used in this disclosure, means exactly equal or one or more deviations from exactly equal that do not significantly impact inspection of a weld of a gasket as described herein.

Further, similar to the first phase 610, at the second phase 620, the first injection port 516 and the second injection portion 518 may provide coupling fluid between the ultrasonic probe 520 and the tube portion 238 of the gasket 230.

Further still, similar to the first phase 610, at the second phase 620, the ultrasonic probe 520 may transmit a plurality of ultrasonic waves 615b through coupling fluid into the tube portion 238 of the gasket 230. The plurality of the ultrasonic waves 615b may travel in the tube portion 238 through the first portion of the weld 237.

Figure 6C:
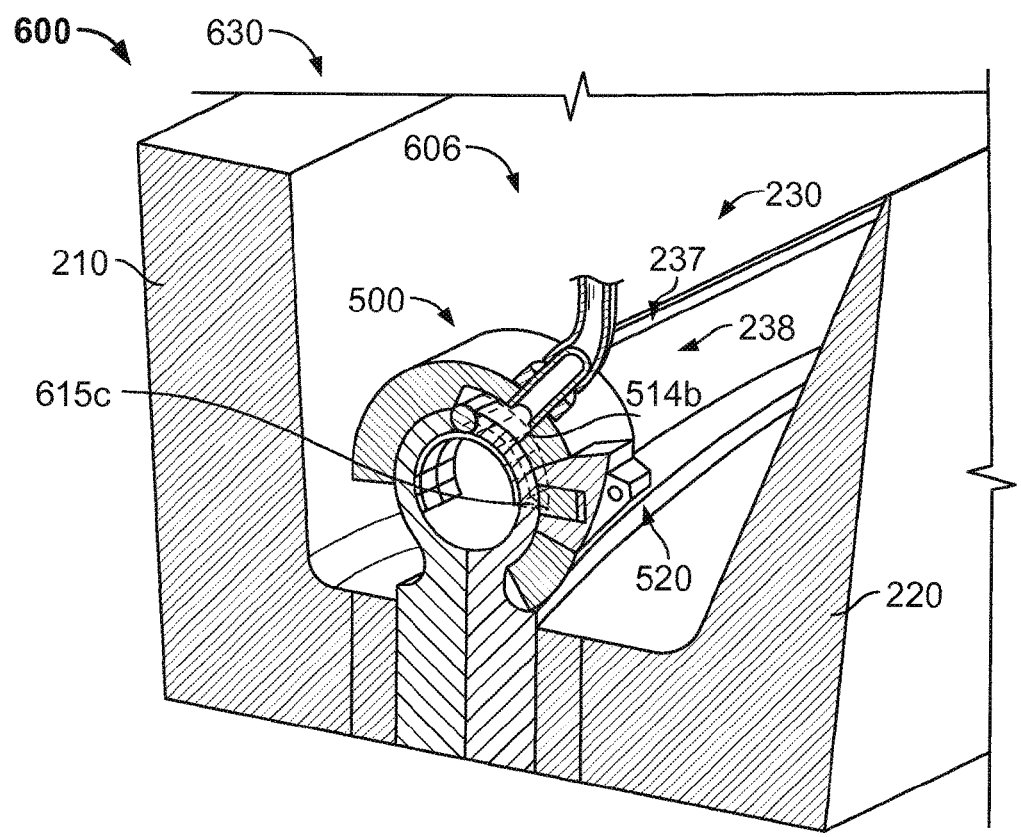
FIG. 6C shows a third phase of an example inspection of a weld of a gasket.

FIG. 6C shows a third phase 630 of the example 600, according to an example embodiment. In the third phase 630, the fixture 500 may be positioned over the portion of the tube portion 238 of the gasket 230 in a third orientation 606. The fixture 500 may be moved from the second orientation 604 to the third orientation 606 by rotating the fixture 500 in a direction opposite the circumferential direction 618. In some embodiments, the fixture 500 may be rotated in the direction opposite the circumferential direction 618 clockwise from the first flange 210 toward the second flange 220.

In the third orientation 606, the first end 514a of the rotational guide 514 may be closer to the weld 237 than the second end 514b of the rotational guide 514. In some embodiments, the third orientation 606 may be the same as or similar to the first orientation 602.

Further, similar to the first phase 610 and the second phase 620, at the third phase 630, the first injection port 516 and the second injection portion 518 may provide the coupling fluid between the ultrasonic probe 520 and the tube portion 238 of the gasket 230.

Further still, similar to the first phase 610 and the second phase 620, at the third phase 630, the ultrasonic probe 520 may transmit a plurality of ultrasonic waves 615c through the coupling fluid into the tube portion 238 of the gasket 230. The plurality of the ultrasonic waves 615b may travel in the tube portion 238 through the first portion of the weld 237.

Figure 6D:
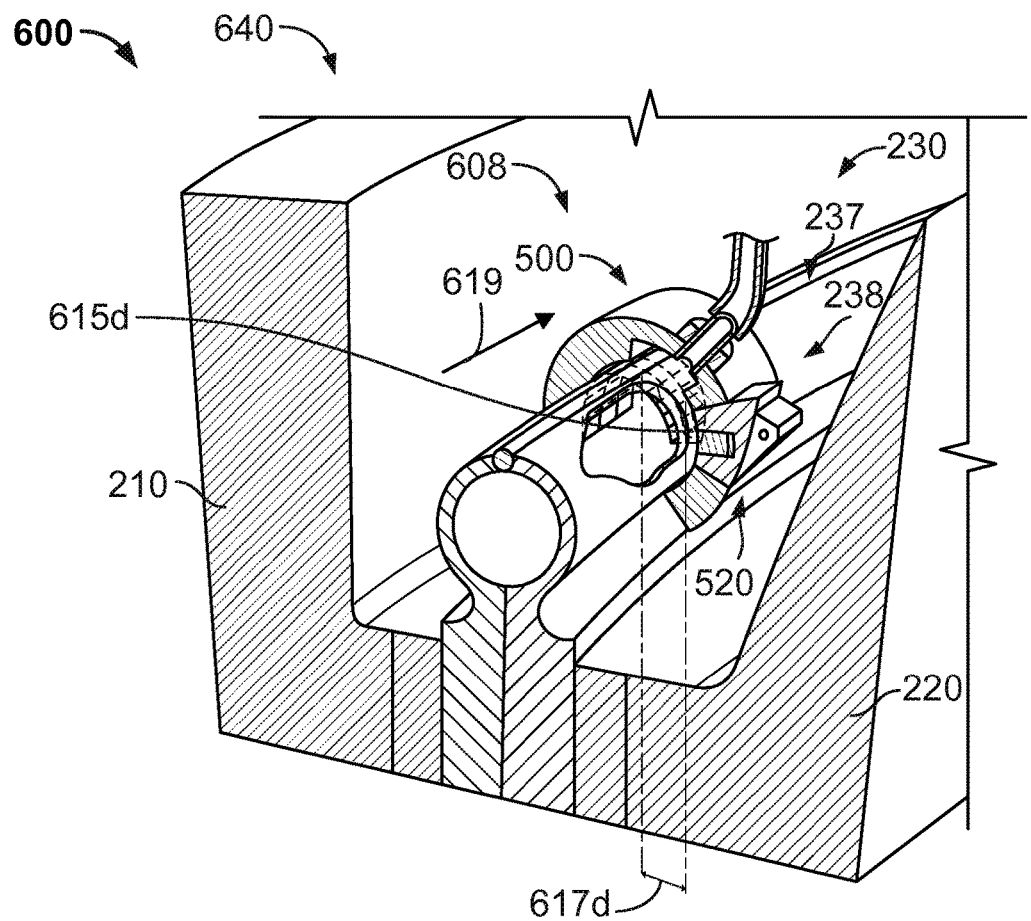
FIG. 6D shows a fourth phase of an example inspection of a weld of a gasket.

FIG. 6D shows a fourth phase 640 of the example 600, according to an example embodiment. In the fourth phase 640, the fixture 500 may be positioned over another portion of the tube portion 238 of the gasket 230 in a fourth orientation 608. The fixture 500 may be moved from the third orientation 606 to the fourth orientation 608 by translating the fixture 500 in a longitudinal direction 619 along the tube portion. In some embodiments, the fixture 500 may be moved from the third orientation 606 to the fourth orientation 608 by translating the fixture a predetermined distance in the longitudinal direction 619. Moreover, in some embodiments, the predetermined distance may be a width dimension of the transducer 544.

In the fourth orientation 608, the second end 514b of the rotational guide 514 may be located a predetermined distance 617d from the weld 237. In some embodiments, the predetermined distance 617d may be substantially equal to the predetermined distance 617a and/or the predetermined distance 617b. Moreover, in some embodiments, in the fourth orientation 608, the first end 514a of the rotational guide 514 may contact a portion of the weld 237.

Further, similar to the first phase 610, the second phase 620, and the third phase 630, at the fourth phase 640, the first injection port 516 and the second injection portion 518 may provide coupling fluid between the ultrasonic probe 520 and the tube portion 238 of the gasket 230.

Further still, similar to the first phase 610, the second phase 620, and the third phase 630, at the fourth phase 640, the ultrasonic probe 520 may transmit a plurality of ultrasonic waves 615*d* through the coupling fluid into the tube portion 238 of the gasket 230. The plurality of the ultrasonic waves 615*d* may travel in the tube portion 238 through a second portion of the weld 237.

As shown in FIGS. 6A-6D, in phases 602-608, the ultrasonic probe 520 may be positioned to closer to the second flange 220 than the first flange 210. Moreover, during phases 602-608, the wedge 522 may travel at a predetermined velocity. In some embodiments, the predetermined velocity of the wedge 522 may be between 2 and 3 millimeters per second, such as around 2.4 millimeters per second.

The plurality of ultrasonic waves 615*a* may take various forms. For example, the plurality of ultrasonic waves 615*a* may include shear waves. Moreover, the plurality of ultrasonic waves 615*a* may have various parameters. In some embodiments, the plurality of ultrasonic waves 615*a* may include 16 beams. However, in some embodiments, the plurality of ultrasonic waves 615*a* may include more or less than 16 beams, such as 32 beams. Moreover, in some embodiments, a particular beam of the plurality of ultrasonic waves 615*a* may be spaced apart from another beam of the plurality of ultrasonic waves 615*a* between 0.5 and 1.5 degrees, such as around 0.97 degrees. Further, in some embodiments, the plurality of ultrasonic waves 615*a* may have a predetermined shear velocity. Further still, in some embodiments, the predetermined shear velocity may be between 2 and 4 millimeters per second, such as around 3.24 millimeters per second. Moreover, in some embodiments, the plurality of ultrasonic waves 615*a* may have a predetermined compression velocity. Further, in some embodiments, the predetermined compression velocity may be between 4 and 6 millimeters per second, such as around 5.89 millimeters per second.

In addition, in some embodiments, each beam of the plurality of ultrasonic waves 615*a* may be transmitted at substantially the same time. The term "substantially the same," as used in this disclosure, means exactly the same or one or more deviations from the same that do not significantly impact inspection of a weld of a gasket as described herein.

Moreover, the plurality of the ultrasonic waves 615*a* transmitted by the ultrasonic probe 520 may refract. For example, at least a portion of the ultrasonic waves may refract when leaving the wedge 522 and entering the tube portion 238 of the gasket 230. In some embodiments, at least some beams of the plurality of ultrasonic waves 516*a* may refract between 45 and 75 degrees when leaving the wedge 522 and entering the tube portion 238.

In some embodiments, the plurality of ultrasonic waves 615*b*, the plurality of ultrasonic waves 616*c*, and the plurality of ultrasonic waves 615*d* may each take the form of or be similar in form to the plurality of sound waves 615*a*.

Further, example 600 may include a variety of scan parameters. For example, phases 610-640 may include a scan sweep, a scan length, and an index offset. In some embodiments, the scan sweep may be between 45 and 50 millimeters, such as around 48.89 millimeters. Moreover, in some embodiments, the scan length may be between 15 and 20 millimeters, such as around 19.42 millimeters. Further, in some embodiments, the index offset may be between −0.25 and −0.75 millimeters, such as around −0.48 millimeters.

Phases 610-630 may provide scanning coverage of the first portion of the weld 237. Moreover, after the fixture 500 is positioned in the fourth orientation 608 at phase 640, phases 620 and 630 may be performed to provide scanning coverage of the second portion of the weld 237. Further, a combination of phases 610-640 may be performed to provide scanning coverage of the weld 237.

In some embodiments, the phases 610-630 may provide a full (or complete) scanning coverage of the first portion of the weld 237. With this arrangement, example 600 may enable a full volumetric inspection of the first portion of the weld 237. Similarly, in some embodiments, after the fixture 500 is positioned in the fourth orientation 608 at phase 640, phases 620 and 630 may be performed to provide full scanning coverage of the second portion of the weld 237. With this arrangement, example 600 may enable a full volumetric inspection of the second portion of the weld 237. Further, a combination of phases 610-640 may be performed to provide full scanning coverage of the weld 237 so as to provide a full volumetric inspection of the weld 237. Accordingly, a combination of phases 610-640 may be performed for an ultrasonic inspection of the weld 237.

In some embodiments, a defect in the weld 237 may be determined based on the scanning with the ultrasonic probe 520. For example, a portion of the weld 237 may reflect ultrasonic waves transmitted by the ultrasonic probe 520, and a determination that the portion of the weld 237 has a defect may be based on the reflected ultrasonic waves received by the ultrasonic probe 520. Moreover, a determination of a size of the defect in the portion of the weld 237 may be based on the reflected ultrasonic waves received by the ultrasonic probe 520. Further, a determination of a location of the defect in the portion of the weld 237 may be based on the reflected ultrasonic waves received by the ultrasonic probe 520. In some embodiments, the reflected ultrasonic waves received by the ultrasonic probe 520 may indicate the portion of the weld has a defect, the size of the defect in the portion of the weld, and/or the location of the defect in the portion of the weld 237. After a defect has been detected in the weld 237, the defect may be repaired and/or the weld 237 may be replaced.

In some embodiments, phase 610 may be performed at a first time period, phase 620 may be performed at a second time period, phase 630 may be performed at a third time period, and phase 640 may be performed at a fourth time period. Moreover, in some embodiments, phases 610-640 may be performed in a substantially consecutive sequence. The term "substantially consecutive," as used in this disclosure, means exactly continuous or one or more deviations from exactly continuous that do not significantly impact inspection of a weld of a gasket as described herein.

Example 600 may be performed in a variety of situations. For instance, example 600 may performed before the equipment 205 is put in service for the first time. Moreover, example 600 may be performed after the equipment 205 is taken out of service. In some embodiments, as shown in FIGS. 6A-6D, example 600 may be performed before the plurality of fasteners 240 is installed between the first flange 210 and the second flange 220. Moreover, in some embodiments, example 600 may be performed after the plurality of fasteners 240 is installed between the first flange 210 and the second flange 220. In some embodiments, when the plurality of fasteners 240 takes the form of a plurality of bolts with nuts, the plurality of fasteners 240 is installed when the plurality of bolts is torqued.

Further, example 600 and/or a combination of phases 610-640 may be performed in connection with other non-destructive testing techniques. For instance, before the plurality of fasteners 240 is installed between the first flange 210 and the second flange 220, a florescent liquid penetrant inspection of the weld 237 may be performed before example 600 is performed. Moreover, before the plurality of fasteners 240 is installed between the first flange and the second flange 220, a florescent liquid penetrant inspection of a component of the weld 237 (e.g., the root 320) may be performed before example 600 is performed. As another example, before the plurality of fasteners 240 is installed between the first flange 210 and the second flange 220, a surface eddy current inspection of the weld 237 may be performed after a combination of phases 610-640 is performed. As yet another example, after the plurality of fasteners 240 is installed between the first flange 210 and the second flange 220, a surface eddy current inspection of the weld 237 may be performed after a combination of phases 610-640 is performed.

FIG. 7 shows a fixture 700 positioned over the portion of the tube portion 238 of the gasket 230, according to an example embodiment. The fixture 700 may be used in connection with example 600. Components of the fixture 700 of FIG. 7 may have the same arrangement and function in a similar manner as the same or similarly numbered components of the fixture 500 in FIG. 5. The fixture 700 is similar to the fixture 500, except that the fixture 700 is coupled to a motor 710 by a connection 712. The connection 712 couples the motor 710 to the body 510.

The fixture 700 may be configured to rotate via the motor 710. For example, the fixture 700 may be configured to rotate in the direction 542 and/or the direction that is opposite the direction 542 via the motor 710. Moreover, the fixture 700 may be configured to translate via the motor. For example, the fixture may be configured to translate in the direction 544 and/or the direction that is opposite the direction 544 via the motor 710.

The motor 710 may comprise any suitable motor for rotating and/or translating the fixture 700. In some embodiments, the motor 710 may include a drive mechanism suitable for rotating and/or translating the fixture 700. The connection 710 may be any suitable wired or wireless connection for coupling the motor 710 to the fixture 700. In some embodiments, the motor 710 may be physically located on the body 510. However, in other embodiments, the motor 510 might not be physically located on the body 410.

The fixture 700, the ultrasonic probe 520, and the motor 710 may define a system 750.

Example 4

Methods

Figure 8:
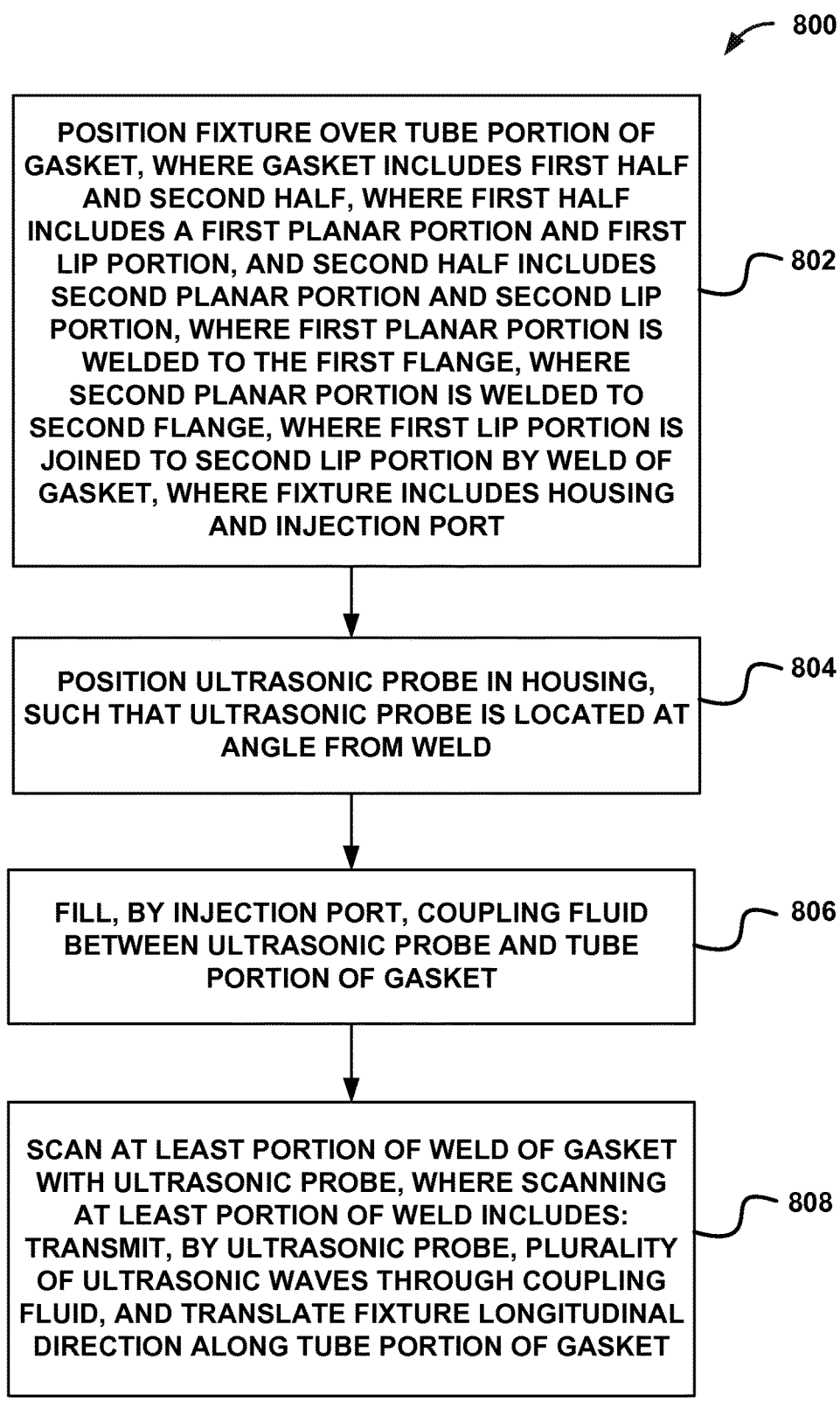
FIG. 8 shows a method for inspection of a weld of a gasket, according to an example embodiment.

FIG. 8 shows a method 800 for inspecting a weld of a gasket, according to an example embodiment. Method 800 begins at block 802 with positioning a fixture over a portion of a tube portion of a gasket. The gasket may include a first half and a second half, where the first half may include a first planar portion and a first lip portion, where the second half may include a second planar portion and a second lip portion, where the first planar portion may be welded to a first flange, the second planar portion may be welded to a second flange, the first lip portion may be joined to the second lip portion by a weld of the gasket and the first lip portion may be joined to the second lip portion defines the tube portion of the gasket, where the fixture includes a housing and an injection port.

In some embodiments, the fixture may take the form of or be similar in form to the fixture 500 and/or the fixture 700. Moreover, in some embodiments, the gasket may take the form the gasket 230. Further, in some embodiments, the first flange may take the form of or be similar in form to the first flange 210. Further still, in some embodiments, the second flange may take the form of or be similar in form to the second flange 220. Moreover, in some embodiments, the first flange may be coupled to a shell portion of a heat exchanger, and the second flange may be coupled to a channel portion of the heat exchanger. Further in some embodiments, the heat exchanger may take the form of or be similar in form to the heat exchanger 100, the shell portion may take the form of or be similar in form to the shell 110, and the channel portion may take the form of or be similar in form to the first channel 120. Further, in some embodiments, the weld may include a seal weld.

Moreover, method 800 continues at block 804 with positioning an ultrasonic probe in the housing, such that the ultrasonic probe is located at an angle from the weld. In some embodiments, the ultrasonic probe may take the form of or be similar in form to the ultrasonic probe 520. Moreover, in some embodiments, the ultrasonic probe may include an ultrasonic phased array probe, and the ultrasonic phased array probe may include a wedge and a transducer. Further, in some embodiments, positioning the ultrasonic probe in the housing may involve positioning the wedge in the housing. Further still, in some embodiments, the ultrasonic probe may be positioned closer to the second flange than the first flange.

Further, method 800 continues at block 806 with filling, by the injection port, coupling fluid between the ultrasonic probe and the tube portion of the gasket. In some embodiments, the coupling fluid may include water.

Further still, method 800 continues at block 808 with scanning at least a portion of the weld of the gasket with the ultrasonic probe. Further, scanning the at least a portion of the weld may involve: transmitting, by the ultrasonic probe, a plurality of ultrasonic waves through the coupling fluid into the tube portion of the gasket, and translating the fixture in a longitudinal direction along the tube portion of the gasket.

In some embodiments, scanning the weld may further involve rotating the fixture in a circumferential direction along the tube portion of the gasket. Moreover, in some embodiments, scanning the weld may further involve rotating the fixture in a circumferential direction along the tube portion of the gasket. Further, in some embodiments, rotating the fixture in the circumferential direction may involve rotating the fixture in the circumferential direction around 0.600 inches. Further still, in some embodiments, scanning the weld further comprises rotating the fixture in a second circumferential direction opposite the circumferential direction. In addition, in some embodiments, translating the fixture in the longitudinal direction along the tube portion may involve translating the fixture in the longitudinal direction around 0.500 inches.

Moreover, in some embodiments, the fixture may be coupled to a motor, and rotating the fixture in the circumferential direction may involve rotating the fixture in the circumferential direction with the motor. Further, in some embodiments, the fixture may be coupled to a motor, and translating the fixture in the longitudinal direction may involve translating the fixture in the longitudinal direction with the motor. Further still, in some embodiments, method 800 may further involve determining a defect in the at least a portion of the weld of the gasket based on scanning the at least portion of the weld.

Examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to the skilled artisan.

It is understood that the invention is not limited to the particular methodology, protocols, etc., described herein, as these may vary as the skilled artisan will recognize. It is also to be understood that the terminology used herein is used for the purpose of describing particular embodiments only, and is not intended to limit the scope of the invention. It also is to be noted that, as used herein and in the appended claims, the singular forms "a," "an," and "the" include the plural reference unless the context clearly dictates otherwise. Thus, for example, a reference to "a fixture" is a reference to one or more fixtures and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Particular methods, devices, and materials are described, although any methods and materials similar or equivalent to those described herein can be used in the practice or testing of the invention. The disclosures of all references and publications cited above are expressly incorporated by reference in their entireties to the same extent as if each were incorporated by reference individually.

What is claimed is:

1. A method comprising:
    positioning a fixture over a portion of a tube portion of a gasket, wherein the gasket comprises a first half and a second half, wherein the first half comprises a first planar portion and a first lip portion, and the second half comprises a second planar portion and a second lip portion, wherein the first planar portion is welded to a first flange, wherein the second planar portion is welded to a second flange, wherein the first lip portion is joined to the second lip portion by a weld of the gasket and the first lip portion joined to the second lip portion defines the tube portion of the gasket, wherein the fixture comprises a housing and an injection port;
    positioning an ultrasonic probe in the housing, such that the ultrasonic probe is located at an angle from the weld;
    filling, by the injection port, coupling fluid between the ultrasonic probe and the tube portion of the gasket; and
    scanning at least a portion of the weld of the gasket with the ultrasonic probe, wherein scanning the at least a portion of the weld comprises:
        transmitting, by the ultrasonic probe, a plurality of ultrasonic waves through the coupling fluid into the tube portion of the gasket, and
        translating the fixture in a longitudinal direction along the tube portion of the gasket.

2. The method of claim 1, wherein the first flange is coupled to a shell portion of a heat exchanger, and wherein the second flange is coupled to a channel portion of the heat exchanger.

3. The method of claim 1, wherein the weld comprises a seal weld.

4. The method of claim 1, wherein the ultrasonic probe comprises an ultrasonic phased array probe, and wherein the ultrasonic phased array probe comprises a wedge and a transducer.

5. The method of claim 4, wherein positioning an ultrasonic probe in the housing comprises positioning the wedge in the housing.

6. The method of claim 1, wherein the ultrasonic probe is positioned closer to the second flange than the first flange.

7. The method of claim 1, wherein the coupling fluid comprises water.

8. The method of claim 1, wherein scanning the weld further comprises rotating the fixture in a circumferential direction along the tube portion of the gasket.

9. The method of claim 8, wherein rotating the fixture in the circumferential direction comprises rotating the fixture in the circumferential direction around 0.600 inches.

10. The method of claim 8, wherein rotating the fixture in the circumferential direction comprises rotating the fixture counterclockwise toward the first flange.

11. The method of claim 8, wherein scanning the weld further comprises rotating the fixture in a second circumferential direction opposite the circumferential direction.

12. The method of claim 1, wherein translating the fixture in the longitudinal direction along the tube portion comprises translating the fixture in the longitudinal direction around 0.500 inches.

13. The method of claim 1, wherein the fixture is coupled to a motor, and wherein rotating the fixture in the circumferential direction comprises rotating the fixture in the circumferential direction with the motor.

14. The method of claim 1, wherein the fixture is coupled to a motor, and wherein translating the fixture in the longitudinal direction comprises translating the fixture in the longitudinal direction with the motor.

15. The method of claim 1, further comprising determining a defect in the at least a portion of the weld of the gasket based on scanning the at least portion of the weld with the ultrasonic probe.

16. A system comprising:
    a fixture positioned over a portion of a tube portion of a gasket, wherein the gasket comprises a first half and a second half, wherein the first half comprises a first planar portion and a first lip portion, and the second half comprises a second planar portion and a second lip portion, wherein the first planar portion is welded to a first flange, wherein the second planar portion is welded to a second flange, wherein the first lip portion is joined to the second lip portion by a weld of the gasket and the first lip portion joined to the second lip portion defines the tube portion of the gasket, wherein the fixture comprises a housing, a rotational guide, and an injection port; and an ultrasonic probe positioned in the housing, wherein the fixture is configured to rotate in a circumferential direction along the tube portion of the gasket via the rotational guide, and wherein the fixture is configured to translate in a longitudinal direction along the tube portion of the gasket.

17. The system of claim 16, wherein the weld comprises a seal weld.

18. The system of claim 16, wherein the ultrasonic probe comprises an ultrasonic phased array probe.

19. The system of claim 16 further comprising a motor coupled to the fixture, wherein the fixture is configured to rotate in the circumferential direction along the tube portion of the gasket via the rotational guide by the motor.

20. A fixture comprising:
 a housing;
 an injection port; and
 a rotational guide, wherein the fixture is configured to be positioned over a portion of a tube portion of a gasket, wherein the gasket comprises a first half and a second half, wherein the first half comprises a first planar portion and a first lip portion, and the second half comprises a second planar portion and a second lip portion, wherein the first planar portion is welded to a first flange, wherein the second planar portion is welded to a second flange, wherein the first lip portion is joined to the second lip portion by a weld of the gasket and the first lip portion joined to the second lip portion defines the tube portion of the gasket, wherein the fixture is configured to rotate in a circumferential direction along the tube portion of the gasket via the rotational guide, and wherein the fixture is configured to translate in a longitudinal direction along the tube portion of the gasket.

\* \* \* \* \*